(12) United States Patent
Abadie et al.

(10) Patent No.: US 8,747,856 B2
(45) Date of Patent: Jun. 10, 2014

(54) ANTIGEN BINDING FRAGMENTS OF AN ANTIBODY FOR USE IN TREATING OR DIAGNOSING OCULAR DISEASES

(75) Inventors: Claire Abadie, Annecy (FR); Jean-Marc Combette, Saint-Cergues (FR); Catherine Deloche, Geneva (CH); Robert Anthony Williamson, La Jolla, CA (US)

(73) Assignee: Ribovax Biotechnologies S.A., Petit-Lancy (CH)

( * ) Notice: Subject to any disclaimer, the term of this patent is extended or adjusted under 35 U.S.C. 154(b) by 25 days.

(21) Appl. No.: 13/318,805

(22) PCT Filed: May 4, 2010

(86) PCT No.: PCT/EP2010/056047
§ 371 (c)(1),
(2), (4) Date: Mar. 16, 2012

(87) PCT Pub. No.: WO2010/128053
PCT Pub. Date: Nov. 11, 2010

(65) Prior Publication Data
US 2012/0165512 A1    Jun. 28, 2012

(30) Foreign Application Priority Data

May 4, 2009  (EP) .................................... 09159303

(51) Int. Cl.
| | |
|---|---|
| *C07K 16/00* | (2006.01) |
| *C07K 16/08* | (2006.01) |
| *A61K 9/00* | (2006.01) |
| *A61K 39/00* | (2006.01) |
| *A61K 39/245* | (2006.01) |

(52) U.S. Cl.
CPC ........... *A61K 39/00* (2013.01); *A61K 2039/505* (2013.01); *A61K 2201/01* (2013.01); *C07K 16/085* (2013.01); *C07K 16/087* (2013.01); *C07K 16/08* (2013.01); *C07K 16/00* (2013.01); *A61K 2039/55511* (2013.01); *A61K 2121/00* (2013.01)
USPC ................... 424/159.1; 530/387.1; 530/389.4; 530/391.3; 530/300; 424/130.1; 424/184.1; 424/229.1; 424/231.1; 424/147.1; 424/9.2; 424/78.04; 424/78.07; 604/521; 604/289; 604/294

(58) Field of Classification Search
CPC ........ C07K 16/00; C07K 16/08; A61K 39/12; C12Q 1/70; C12Q 1/705; C12Q 16/081; G01N 33/53; G01N 33/6854
USPC .......................... 530/389.4, 300, 387.1, 391.3
See application file for complete search history.

(56) References Cited

U.S. PATENT DOCUMENTS

| | | | | |
|---|---|---|---|---|
| 5,846,746 | A * | 12/1998 | Gipson ........................ | 435/7.21 |
| 6,156,313 | A * | 12/2000 | Burton et al. ............... | 424/147.1 |
| 2005/0191293 | A1* | 9/2005 | Deshpande et al. ........ | 424/143.1 |
| 2007/0089201 | A1* | 4/2007 | Briggs et al. ................ | 800/288 |
| 2010/0028406 | A1* | 2/2010 | Kalia et al. .................. | 424/443 |
| 2011/0033389 | A1* | 2/2011 | Chen et al. .................. | 424/9.6 |

FOREIGN PATENT DOCUMENTS

| | | |
|---|---|---|
| GB | 1492383 A | 11/1977 |
| WO | WO-97/26329 A1 | 7/1997 |
| WO | WO-03/091413 A2 | 11/2003 |
| WO | WO-2004/050838 A2 | 6/2004 |
| WO | WO-2005/023303 A1 | 3/2005 |

OTHER PUBLICATIONS

Berdugo M, Larsen IV, Abadie C, Deloche C, Kowalczuk L, Touchard E, Dubietzig R, Brandt CR, Behar-Cohen F, Combette JM. Ocular distribution, spectrum of activity, and in vivo viral neutralization of a fully humanized anti-herpes simplex virus IgG Fab fragment following topical application. Antimicrob Agents Chemother, Mar. 2012;56(3):1390-402.*
De Logu A, Williamson RA, Rozenshteyn R, Ramiro-Ibañez F, Simpson CD, Burton DR, Sanna PP. Characterization of a type-common human recombinant monoclonal antibody to herpes simplex virus with high therapeutic potential. J Clin Microbiol. Nov. 1998;36(11):3198-204.*
Epstein SP, Nurozler M, Smetana CR, Asbell PA. Efficacy of polyclonal antibodies for treatment of ocular herpes simplex infection. Cornea. Jul. 2001;20(5):495-500.*
Shimmura S, Ono M, Shinozaki K, Toda I, Takamura E, Mashima Y, Tsubota K. Sodium hyaluronate eyedrops in the treatment of dry eyes. Br J Ophthalmol. Nov. 1995;79(11):1007-11.*
Williams KA, Brereton HM, Farrall A, Standfield SD, Taylor SD, Kirk LA, Coster DJ. Topically applied antibody fragments penetrate into the back of the rabbit eye. Eye (Lond). Aug. 2005;19(8):910-3.*
Goni FR, Chen PP, McGinnis D, Arjonilla ML, Fernandez J, Carson D, Solomon A, Mendez E, Frangione B. Structural and idiotypic characterization of the L chains of human IgM autoantibodies with different specificities. J Immunol. May 1, 1989;142(9):3158-63. Erratum in: J Immunol Dec. 1, 1989;143(11):3864.*
Rudikoff S, Giusti AM, Cook WD, Scharff MD. Single amino acid substitution altering antigen-binding specificity. Proc Natl Acad Sci U S A. Mar. 1982;79(6):1979-83.*
Rector JT, Lausch RN, Oakes JE. Use of monoclonal antibodies for analysis of antibody-dependent immunity to ocular herpes simplex virus type 1 infection. Infect Immun. Oct. 1982;38(1):168-74.*
Allansmith et al., The dynamics of IgG in the cornea, Invest. Ophthalmol. Vis. Sci., 18:947-55 (1979).
Extended European Search Report, EP 09159303.8, dated Jul. 14, 2009.
International Search Report and Written Opinion for corresponding International application No. PCT/EP2010/056047, mailing date Jul. 9, 2010.
International Preliminary Report on Patentability for International application No. PCT/EP2010/056047, dated Jun. 1, 2011.
Su et al., Protective antibody therapy is associated with reduced chemokine transcripts in herpes simplex virus type 1 corneal infection, J. Virol., 70(2):1277-81 (1996).

* cited by examiner

*Primary Examiner* — Benjamin P Blumel
*Assistant Examiner* — Rachel Gill
(74) *Attorney, Agent, or Firm* — Marshall, Gerstein & Borun LLP

(57) ABSTRACT

The present invention relates to the use of a fully human antigen binding fragment of an antibody for the manufacture of a medicament for the treatment or diagnosis of an ocular disease upon topical administration. The invention further relates to a pharmaceutical composition comprising a fully human binding fragment of an antibody for ocular topical administration for treatment or diagnosis of an ocular disease. In particular, the antibody neutralizes HSV1 and HSV2.

5 Claims, 9 Drawing Sheets

SEQUENCE LISTING

```
<160> NUMBER OF SEQ ID NOS: 4

<210> SEQ ID NO 1
<211> LENGTH: 231
<212> TYPE: PRT
<213> ORGANISM: homo sapiens

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ser Phe Ser Ser Tyr
            20                  25                  30

Ala Ile Asn Trp Val Arg Gln Ala Pro Gly Gln Gly Leu Glu Trp Met
        35                  40                  45

Gly Gly Leu Met Pro Ile Phe Gly Thr Thr Asn Tyr Ala Gln Lys Phe
    50                  55                  60
```

```
Gln Asp Arg Leu Thr Ile Thr Ala Asp Val Ser Ser Thr Ala Tyr
 65                  70                  75                  80

Met Gln Leu Ser Gly Leu Thr Tyr Glu Asp Thr Ala Met Tyr Tyr Cys
                 85                  90                  95

Ala Arg Val Ala Tyr Met Leu Glu Pro Thr Val Thr Ala Gly Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr
225                 230

<210> SEQ ID NO 2
<211> LENGTH: 214
<212> TYPE: PRT
<213> ORGANISM: homo sapiens

<400> SEQUENCE: 2

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ala
                 20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Arg Ser Pro
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

-continued

```
Ala Cys Glu Val Thr His Gln Gly Leu Ser Ser Pro Val Thr Lys Ser
        195                 200                 205
Phe Asn Arg Gly Glu Cys
    210

<210> SEQ ID NO 3
<211> LENGTH: 125
<212> TYPE: PRT
<213> ORGANISM: homo sapiens

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ser Phe Ser Ser Tyr
            20                  25                  30

Ala Ile Asn Trp Val Arg Gln Ala Pro Gly Gln Gly Leu Glu Trp Met
        35                  40                  45

Gly Gly Leu Met Pro Ile Phe Gly Thr Thr Asn Tyr Ala Gln Lys Phe
    50                  55                  60

Gln Asp Arg Leu Thr Ile Thr Ala Asp Val Ser Thr Ser Thr Ala Tyr
65                  70                  75                  80

Met Gln Leu Ser Gly Leu Thr Tyr Glu Asp Thr Ala Met Tyr Tyr Cys
                85                  90                  95

Ala Arg Val Ala Tyr Met Leu Glu Pro Thr Val Thr Ala Gly Gly Leu
            100                 105                 110

Asp Val Trp Gly Gln Gly Thr Thr Val Thr Val Ser Ser
        115                 120                 125

<210> SEQ ID NO 4
<211> LENGTH: 107
<212> TYPE: PRT
<213> ORGANISM: homo sapiens

<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ala
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Pro
                85                  90                  95

Thr Phe Gly Gly Gly Thr Lys Val Glu Ile Lys
            100                 105
```

ANTIGEN BINDING FRAGMENTS OF AN ANTIBODY FOR USE IN TREATING OR DIAGNOSING OCULAR DISEASES

CROSS-REFERENCE TO RELATED APPLICATIONS

This application is a U.S. National Phase of International Application No. PCT/EP2010/056047 filed May 4, 2010, incorporated herein by reference, which claims priority benefit of European Patent Application No. 09159303.8 filed May 4, 2009.

The present invention relates to the use of antigen binding fragments of an antibody for the manufacture of a medicament for the treatment or diagnosis of an ocular disease upon topical administration.

STATE OF THE ART

HSV is a DNA virus that commonly affects humans. Infection occurs by direct contact of skin or mucous membrane with virus-laden lesions or secretions. HSV type 1 (HSV-1) is primarily responsible for orofacial and ocular infections, whereas HSV type 2 (HSV-2) generally is transmitted sexually and causes genital disease. HSV-2 may infect the eye by means of orofacial contact with genital lesions and occasionally is transmitted to neonates as they pass through the birth canal of a mother with genital HSV-2 infection.

Primary HSV-1 infection occurs most commonly in the mucocutaneous distribution of the trigeminal nerve. It is often asymptomatic but may manifest as a nonspecific upper respiratory tract infection. After the primary infection, the virus spreads from the infected epithelial cells to nearby sensory nerve endings and is transported along the nerve axon to the cell body located in the trigeminal ganglion. There, the virus genome enters the nucleus of a neuron, where it persists indefinitely in a latent state. Primary infection of any of the 3 (i.e. ophthalmic, maxillary, mandibular) branches of cranial nerve V can lead to latent infection of nerve cells in the trigeminal ganglion. Interneuronal spread of HSV within the ganglion allows patients to develop subsequent ocular disease without ever having had primary ocular HSV infection.

Recurrent ocular HSV infection has traditionally been thought of as reactivation of the virus in the trigeminal ganglion, which migrates down the nerve axon to produce a lytic infection in ocular tissue. Evidence suggests that the virus may also subsist latently within corneal tissue, serving as another potential source of recurrent disease and causing donor-derived HSV disease in transplanted corneas.

HSV infection is ubiquitous, with an estimated one third of the population worldwide suffering from recurrent infections. Only in the United States, approximately 20,000 new cases of ocular HSV and more than 28,000 reactivations occur annually.

Herpes simplex virus infections of the eye are the leading cause of blindness due to infectious disease in developed countries.

Herpes simplex virus infections of the eye may more in particular be divided into 4 categories: infectious epithelial keratitis, neurotrophic keratopathy, stromal keratitis, and endotheliitis.

Diagnosis is usually made on clinical grounds on the basis of characteristic features of the corneal lesion and by exclusion. Laboratory studies may help confirm the clinical suspicion in cases lacking typical findings, but they are not readily available in most clinical settings. Epithelial scrapings with Giemsa stain may show multinucleated giant cells, resulting from coalescence of infected corneal epithelial cells and intranuclear viral inclusions. However, negative cytology results do not exclude HSV infection. Viral cultures have a good sensitivity but take several days to reach a result. HSV antigen detection tests, such as the enzyme-linked virus inducible system (ELVIS), are specific but are limited by their lower sensitivity. Cell culture for confirmation of HSV is therefore in any case recommended when the ELVIS test result is negative again leading to a time-consuming procedure. Polymerase chain reaction using tear samples, corneal epithelium, anterior chamber tap, or corneal buttons may detect viral DNA in cases of herpetic keratitis or keratouveitis. However, it does not distinguish between latent or active HSV infections. Diagnosis is especially difficult in the case of disciform endotheliitis or stromal disease, as virus particles are often not found in stromal biopsy specimens and no cultures can therefore be obtained.

As far as treatment is concerned, in spite of the availability of antivirals for therapy, this disease remains a significant health problem. In Europe, "Zovirax®" (acyclovir) ointment is approved for treating ocular infections (although emergence of drug resistant strains is causing concern). Corneal damage is however not prevented by acyclovir. In the United States, "Viroptic®" (trifluorothymidine 1% aqueous solution) is the only approved drug for these infections. Both acyclovir and trifluorothymidine have reduced efficacy against recurrent disease, which is the usual cause of corneal clouding leading to blindness. Significant side effects can occur with the use of both preparations and because of the formulations, there are issues with patient compliance. Clearly, improved therapeutic or diagnostic strategies are needed for HSV ocular diseases.

Antibodies are increasingly used in diagnostics and therapeutics of various diseases. The use of antibodies would be extremely advantageous in the diagnosis and treatment of diseases such as those described above where alternative treatment is highly unsatisfactory.

Antibodies may be administered systemically although they can cause serious systemic side effects when therapeutic concentrations are reached at the site of infection.

Topical administration of antibodies to modulate immunopathological conditions of the cornea or anterior segment would be advantageous to avoid these side effects, but it is ineffective because whole antibodies are too large to penetrate the cornea rapidly (Allansmith M, de Ramus A, Maurice D. The dynamics of IgG in the cornea. Invest Ophthalmol V is Sci 1979; 18:947-55).

It is an object of the present invention to provide the use of a fully human antigen binding fragment of an antibody having a sequence with at least 90% homology to SEQ ID NO:3 and/or SEQ ID NO:4 for the manufacture of a medicament for the treatment or diagnosis of an ocular disease upon topical administration.

It is a further object of the present invention to provide the use of a fully human antigen binding fragment of an antibody having a sequence with at least 90% homology to SEQ ID NO:1 and SEQ ID NO:2 for the manufacture of a medicament for the treatment or diagnosis of an ocular disease upon topical administration.

It is a further object of the present invention to provide a pharmaceutical composition for ocular topical administration for the treatment and/or the diagnosis of an ocular disease comprising a fully human binding fragment of an antibody, characterised in that said fully human antigen binding fragment has a sequence with at least 90% homology to SEQ ID NO:3 and/or SEQ ID NO:4 or a sequence with at least 90% homology to SEQ ID NO:1 and SEQ ID NO:2.

In particular, the antibody neutralises HSV1 and HSV2.

DEFINITIONS

Unless defined otherwise, all technical and scientific terms used herein have the same meaning as commonly understood by one of ordinary skill in the art to which this invention pertains. Although many methods and materials similar or equivalent to those described herein may be used in the practice or testing of the present invention, preferred methods and materials are described below. Unless mentioned otherwise, the techniques described herein for use with the invention are standard methodologies well known to persons of ordinary skill in the art.

By the term "Fab" or "antigen binding fragment" there is intended any antibody fragment that retains the ability to bind to its antigen and includes at least one variable domain of either the light chain or the heavy chain.

By the term "ocular disease" there is intended any infection (primary or secondary) such as for example ocular keratitis (epithelial and stromal), blepharitis, conjunctivitis, blepharoconjuntivitis, ulcerations.

By the term "retention enhancer" there is intended any substance or composition that will prolong the time of residence of the product in the eye compartment affected by the disease, such as sodium hyaluronate, hydroxymethylcellulose, hydroxyethylcellulose, hydroxyethylmethylcellulose, hydroxypropylmethylcellulose, vinylpolyalcohol, xantan gum, gellan gum, chitosan, polylactic acid and derivatives thereof.

By the term "pharmaceutical composition" there is intended any therapeutically acceptable mixture or combination of substances.

BRIEF DESCRIPTION OF THE DRAWINGS

FIG. 2 a: the white square shows the re-epithelialised area of the previous ulcer. FIGS. 2 d and 2 i are respectively higher magnifications of the white squares in FIGS. 2 c and 2 h: sub-epithelial stromal cells are positively labelled for AC-8. FIGS. 2 g and 2 j are higher magnifications of the white squares in 2 f and 2 h respectively, showing the positively AC-8 labelled endothelium. FIG. 2 k-m are the IHC analysis of a control vehicle-treated cornea. Epith=epithelium, Endoth=endothelium. Bar=200 μm.

DETAILED DESCRIPTION OF THE INVENTION

Figure 1A:
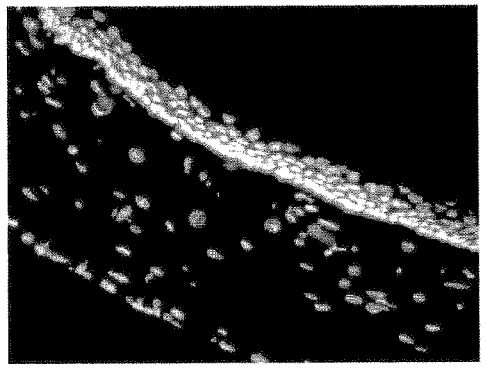
FIG. 1 shows an example of a series of immunohistochemistry images showing the analysis of the cornea (a-h, l-n) and the ciliary body (i-k, o-q) 1 hour after 5 instillations during 4 days then 1 single instillation on the last day of AC-8 (a-k) or 1 hour after 5 instillations during 4 days then 1 single instillation on the last day of PBS (vehicle, l-q). d and h are higher magnifications of the related white squares showing respectively (d) an alexa-labelled dendritiform sub-epithelial cell and (h) the labelled corneal endothelium. Bars=100 μm.
Figure 1B:
Figure 1C:
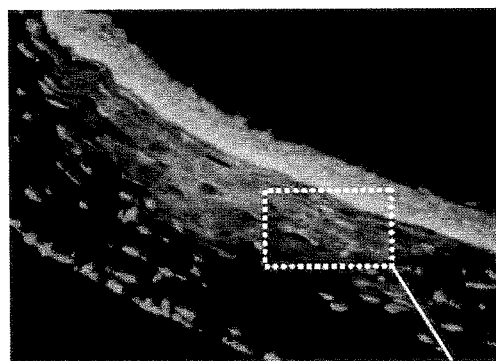

According to the present invention a fully human antigen binding fragment of an antibody having a sequence SEQ ID NO:1 and SEQ ID NO:2 is used for the manufacture of a medicament for the treatment or diagnosis of an ocular disease upon topical administration.

It should be understood that the constant regions of respectively the heavy chain (SEQ ID NO:1) and the light chain (SEQ ID NO:2) may be replaced with any appropriate human immunoglobulin constant region so that the final molecule retains the ability to bind to the antigen.

Thus in an alternative embodiment according to the present invention the scFv with SEQ ID NO:3 or SEQ ID NO:4 can be used for the manufacture of a medicament for the treatment or diagnosis of an ocular disease upon topical administration.

In particular, the antibody of the invention neutralises HSV1 and HSV2. In particular, the viral surface antigen is gD.

The medicament of the invention is preferably formulated with a retention enhancer of the antigen binding fragment into the eye. Retention enhancers useful in the invention may be chosen in the group consisting of sodium hyaluronate, hydroxymethylcellulose, hydroxyethylcellulose, hydroxyethylmethylcellulose, hydroxypropylmethylcellulose, polyvinylalcohol, xanthan gum, gellan gum, chitosan, polylactic acid and derivatives thereof.

The medicament of the present invention is preferably in the form of an eye drop, ointment, gel, ophthalmic cream.

The ocular disease is advantageously ocular keratitis, blepharitis, conjunctivitis, blepharoconjunctivitis, ulcerations.

The fully human antigen binding fragments according to the present invention may be used in methods of diagnosis comprising contacting a portion of the eye with the antigen binding fragments indicative of the condition and detecting the presence of a complex comprising the antigen binding fragment and the antigen. The detection of the complex may be performed according to any technique known in the art, such as the antigen binding fragment having a detectable label associated therewith that may subsequently be detected in immunoassays in vitro and in vivo. Examples of in vitro methods are Enzyme-linked immunosorbent assay ELISA (indirect, sandwich, competitive) and radioimmunoassay (RIA).

The label may be directly or indirectly associated with the antigen binding fragment, or attached to a subsequent reaction product of the antigen binding molecule. The label may be selected from the group including a chromogen, a catalyst, an enzyme, a fluorochrome, a chemiluminescent molecule, a radioisotope and a dye.

According to the present invention a pharmaceutical composition is provided for ocular topical administration for the treatment or diagnosis of an ocular disease comprising a fully human binding fragment of an antibody including SEQ ID NO:1, SEQ ID NO:2, SEQ ID NO:3 or SEQ ID NO:4.

For example a pharmaceutical composition according to the present invention may consist of 15% $H_2O$, 15% white mineral oil, 70% Aquaphor® (ointment) and the Fab fragment of the present invention 1 mg/ml.

The antigen binding fragments of the invention may be obtained by different methods known in the art, for example by the enzymatic digestion with papain of extracted IgGs or by recombinant production in (transient or stable) eukaryotic or prokaryotic expression systems and subsequent affinity purification.

A major advantage of the compositions according to the invention results from the Fabs being fully human, i.e. being encoded by a human polynucleotide sequence. In vivo use of the Fabs of the invention for diagnosis or treatment of HSV diseases greatly reduces the adverse effects due to host immune response to passively administered antibodies which is a significant problem when monoclonal antibodies of xenogeneic or chimeric derivation are used.

Furthermore, Fab fragments are advantageous with respect to whole IgGs because they are not affected by Fc receptors on cells and do not precipitate antigen, they therefore display a reduced immunogenicity and are less susceptible to phagocytosis. Moreover, Fab fragments are more rapidly cleared from tissue than whole IgG molecules.

Fabs are also easier to produce with respect to IgG antibodies in terms of process, costs and time as they can be produced in *E. coli* expression systems.

Fabs are stable and soluble (insolubility being a feature that can enhance immunogenicity). These features allow to obtain high levels of expression and an optimum stability of the drug substance and drug product. The stability of Fabs allows them to display a long half-life.

According to an alternative embodiment of the present invention also single chain Fvs (scFv) are provided.

Figure 6:
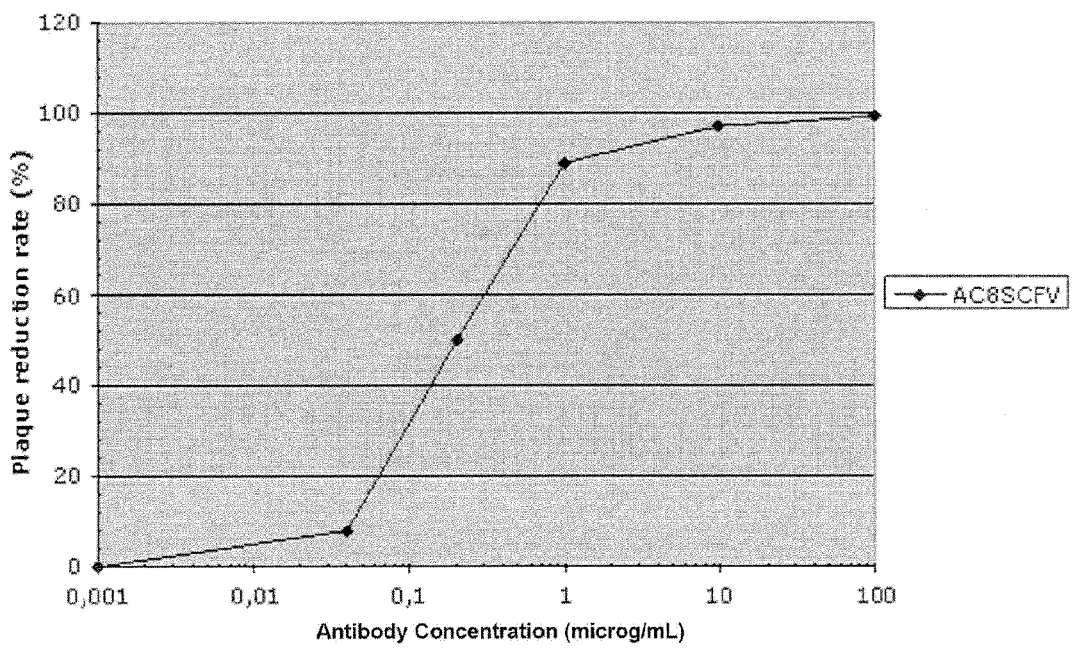
FIG. 6 is a diagram showing the neutralisation of HSV-1 in a plaque reduction assay as a function of increasing concentrations of scFv AC-8.

As shown in FIG. 6 scFv AC-8 is highly efficient in neutralising HSV infectivity in an in-vitro plaque reduction test.

Viral titres measured in tear film samples from mice treated with AC-8 showed effective neutralisation of HSV1 in comparison to an aspecific Fab.

After topical instillation, AC-8 penetrates into the intact eye and can be detected using both immunohistochemistry and Elisa testing at one hour after instillation, in the aqueous humour and in the vitreous. After de-epithelialisation of the cornea, the ocular penetration is enhanced in the aqueous humour and in the vitreous. AC-8 can be visualised in the corneal cells of intact corneas and seems to penetrate in the eyes mostly through a transcleral route. After sub-conjunctival injection, the ocular penetration of AC-8 is similar to that obtained after instillation on a de-epithelialised cornea. However, sub-conjunctival injection on eyes after corneal de-epithelialisation results in a 5 times increase in AC-8 ocular penetration. Immunohistochemistry revealed that AC-8 seemed to accumulate in dendritic sub epithelial cells, demonstrating its corneal penetration. After topical instillation, AC-8 was measured at efficient antiviral concentrations in the ocular media.

EXAMPLES

Example 1

Viral Titres Measured in Tear Film Samples from Mice Treated with AC-8 Showed Effective Neutralisation of HSV1 in Comparison to an Aspecific Fab Treatments of 3 μl each were administered by eyedrop to the infected eye (right). Treatments (AC-8 1 mg/mL or aspecific Fab fragment) began at 8:00 am, 10:00 am, 12:00 pm, 2:00 pm, 4:00 pm, 6:00 pm, 8:00 pm, 10:00 pm starting the morning after infection (day 2) and continued for 7 days. Treatment of the groups proceeded in the same order on each day and were completed within an hour of the start time. Mice were anesthetized with Isofluorane (3-5%) or the equivalent for each treatment. Virus Strain. The ocular isolate CJ394, which causes moderate levels of keratitis with little or no mortality was used. Animals were infected in the right eye with 1×10$^5$ PFU.

Infection Protocol. For infection, BALB/C mice were anesthetized with Ketamine/xylazine. The right cornea was scarified near the limbal margin leaving the central cornea intact. A 5 μl drop of DMEM containing the inoculum was placed on the right cornea and the eye lids were closed 2 times over the cornea and the animals were returned to their cages.

Viral titres. Tear film samples for titrating virus in the right eye were collected on Days 1, 3, 5, 7, 9, 11, and 13 post-infection. Mice were anesthetized briefly for sample collection and returned to their cage. Samples were collected prior to the initiation of treatment on each of the days by placing 10 μl of cell culture medium on the cornea, flushing the liquid 2-3 times with a pipetman and then transferring the liquid to 190 μl of medium for transport to the virology laboratory. The samples were then serially diluted and titrated on Vero cell monolayers. The mice were anesthetized with Isofluorane or the equivalent (3-5%) for collection of tear film samples.

Figure 3:
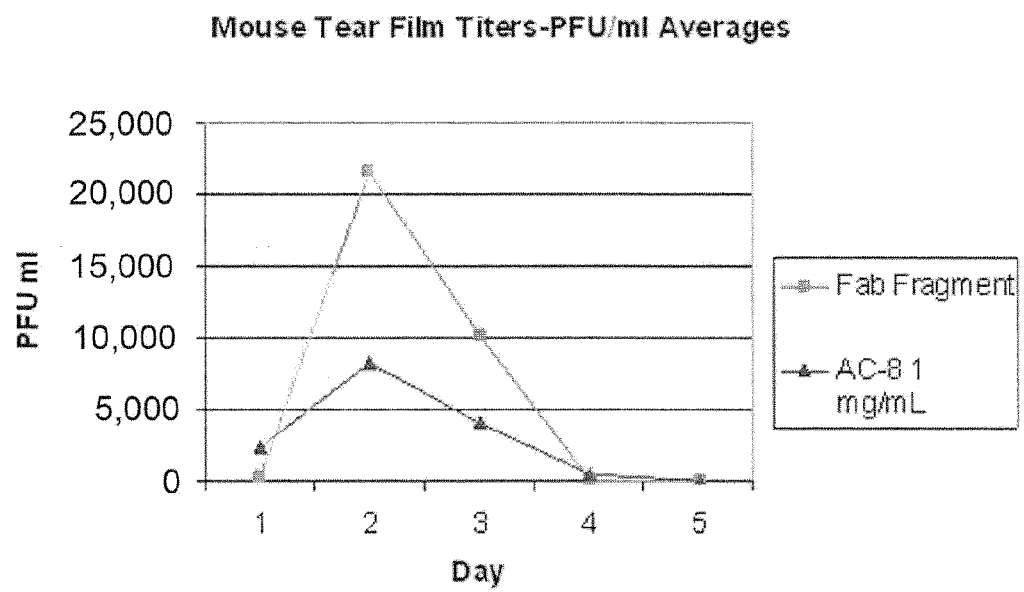
FIG. 3 is a diagram showing the effect of AC-8 on the tear film titres after ocular viral infection in the mouse and therefore demonstrating the neutralisation of HSV by AC-8 in vivo as a function of time.

Results are shown in FIG. 3.

Example 2

AC-8 Penetrates into the Intact Eye and can be Detected by Immunohistochemistry One Hour after Instillation in the Aqueous Humour and in the Vitreous This set of experiments was carried out to evaluate the penetration of AC-8 Fab fragment topically administered. In particular, this experiment was carried out to evaluate the Fab's biodistribution when topically administered onto rat normal corneas.

The substance tested was the Fab fragment at a concentration of 10 μg/mL in PBS. The administration route was by instillation or sub-conjunctival injection in both eyes. The administration volume was 50 μL per instillation using the supplied dropper vial,
50 μL for sub-conjunctival injection using an insulin syringe.

The animals were albinos Lewis rats (6-8 weeks, 120-150 g, Charles River). The animals were kept in conditions validated and approved by the ethical committee of the University of Paris V and the ARVO document concerning the use of animals in experimental ophthalmology. Rats were sacrificed at the end of the in-vivo experiments by a lethal injection of pentobarbital.

For the administrations, the rats were not anesthetized, but gently maintained physically restrained for a few seconds in order to enhance contact time with the cornea. 3 rats per group (6 eyes) were used. Animals were administered as follows:

| Groups (n = 3) | Group code | Adm substance | Administration route | Day 0 | Day 1 | Day 2 | Day 3 | Day 4 | Sacrifice |
|---|---|---|---|---|---|---|---|---|---|
| 1 | H1 | AC-8 Fab | Instillation | 1 | — | — | — | — | Day 0: 1 hour after instillation |
| 2 | H6 | AC-8 Fab | Instillation | 5 (1/hour) | — | — | — | — | Day 0: 1 hour after the 5$^{th}$ instillation |
| 3 | D4 | AC-8 Fab | Instillation | 5 | 5 | 5 | 5 | 1 | Day 4: 1 hour after instillation |
| 4 | SCJ1 | AC-8 Fab | Sub-conjunctival injection | 1 | — | — | — | — | Day 0: 1 hour after injection |

-continued

| Groups (n = 3) | Group code | Adm substance | Administration route | Day 0 | Day 1 | Day 2 | Day 3 | Day 4 | Sacrifice |
|---|---|---|---|---|---|---|---|---|---|
| 5 | SCJ6 | AC-8 Fab | Sub-conjunctival injection | 1 | — | — | — | — | Day 0: 6 hour after injection |
| 6 | D4 PBS | Vehicle | Instillation | 5 | 5 | 5 | 5 | 1 | Day 4: 1 hour after instillation |
| 7 | SCJ PBS | Vehicle | Sub-conjunctival injection | 1 | — | — | — | — | Day 0: 1 hour after injection |

Note 1:
Group 2 was performed to realize a charge dose. One drop per hour is not compatible with a treatment regimen.
Note 2:
Group 3 was performed on a 5 times per day instillation during the awake period, which corresponds to a therapeutic regimen.

Sampling is summarized in the following table:

| Groups 1 to 7 | 1P$^{stP}$ Rat | 2P$^{ndP}$ Rat | 3P$^{rdP}$ Rat | Total samples | Analyses |
|---|---|---|---|---|---|
| Aqueous humour | 2 treated eyes | 2 treated eyes | | 28 | Elisa |
| Vitreous humour | 2 treated eyes | 2 treated eyes | | 28 | Elisa |
| Corneas | 2 treated eyes | 2 treated eyes | | 28 | IHC |
| Complete eye | | | 2 treated eyes | 14 | IHC |
| Serum (gps 4, 5, 7) | 1-2 ml | 1-2 ml | 1-2 ml | 9 | Elisa |

Two rats (4 eyes) of each group (1 to 7) were used to dissect corneas for flat-mounting on object slides. Eyes were dissected on ice. A total of 28 corneas were dissected, and flat-mounted into 24-well plates stored at −80° C.

Both eyes of the third rat of each group (1 to 7, total 14 samples) were placed in OCT® (Optimum Cutting Temperature compound, Tissue-Tek) at −80° C. All the right eyes were used for cryosectioning, and all the left eyes were stored at −80° C. for further use if necessary.

Cryosections were used for immunohistochemical (IHC) analyses with labelled antibodies in order to determine distribution of AC-8 Fab within the cornea layers and the ocular globe.

The frozen cryosections (10 µm) were treated as follows:
fixed 15 minutes in paraformaldehyde 4% at RT,
rinsed twice 10 minutes in PBS 1× at RT,
rinsed 2×10 minutes in PBS-Triton™ X-100 0.1% at RT,
incubated overnight at +4° C. with goat anti-human IgG (Pierce #31132, 1/50 in PBS-Triton™ X-100 0.1%) excepted for the control incubated in PBS 1× only,
rinsed 3×10 minutes in PBS-Triton™×100 0.1% at RT,
incubated 1 hour at +20° C. in the dark with Molecular Probes donkey anti-goat IgG (H+ L) Alexafluor® 594 (red) 1/50,
rinsed twice 10 minutes in PBS 1× at RT,
incubated in DAPI (4',6'-diamidino-2-phenylindole) (blue) 1/5000 in PBS 1×, for nuclear labelling, 5 minutes in the dark at RT,
rinsed 5×5 minutes in PBS 1× at RT,
rinsed once 10 minutes in distilled water at RT and dried,
placed on microscope slides for lecture using a Fluorescence Microscope (Olympus).

In order to have confocal localisation of AC-8 on corneas, IHC was also performed on flat mounted corneas. Optimisation of the IHC protocol was performed on ¼ of the corneas. Sensitivity of the technique could not be optimized sufficiently with the material available, to get well-defined confocal imaging. These results could not be interpreted accurately. This is the reason why complete eye sections were chosen to determine the AC-8 penetration.

The nuclei were stained in blue with DAPI, and the anti-human IgG antibodies, used to reveal AC-8, appear in red (secondary antibody Alexa Fluor® 594-labeled).

Group 1 "H1" (Day 0: 1 instillation of AC-8 10 µg/ml, sacrifice 1 hour after).

No difference in fluorescence is shown between the AC-8 treated eyes (group 1) and the PBS control eyes (group 6) demonstrating that one hour after a single instillation of AC-8 10 µg/ml, no AC-8 penetration is observed into ocular tissues.

Group 2 "H6" (Day 0: 5 instillations of AC-8, 10 µg/ml, sacrifice 1 hour after).

When AC-8 is instilled every hour for 5 hours and sacrifice is performed one hour after the last instillation, AC-8 is detected in the periphery of the cornea as dots that could correspond to engulfment of AC-8 in dendritic cells, which are located in the sub-epithelial stroma. In the centre of the cornea, staining is also observed in the stroma as a diffuse signal as well as patchy signals. In the ciliary body and the retina, a diffuse but mild staining can be detected when compared to the PBS treated rats (group 6).

Group 3 "D4" (Day 0 to Day 3: 5 instillations per day of AC-8, 10 µg/ml, Day 4: 1 instillation, sacrifice 1 hour after).

Figure 1D:
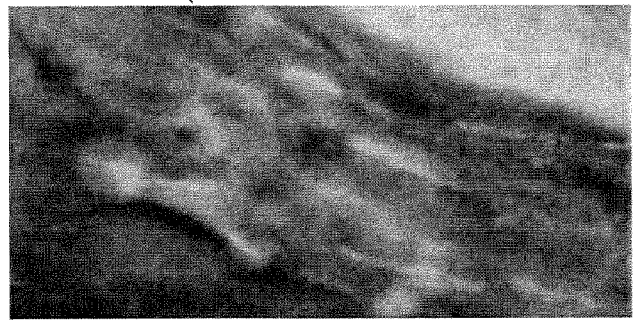
Figure 1E:
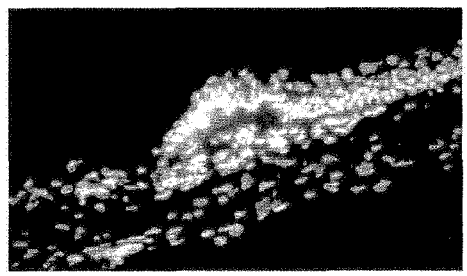
Figure 1F:
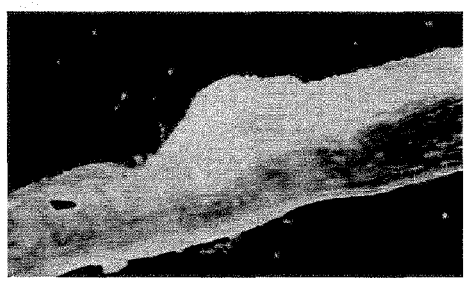
Figure 1G:
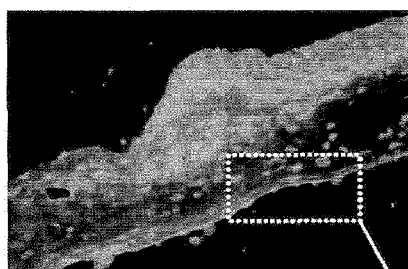
Figure 1H:
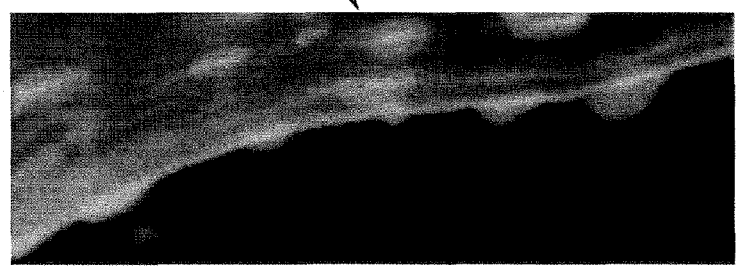
Figure 1I:
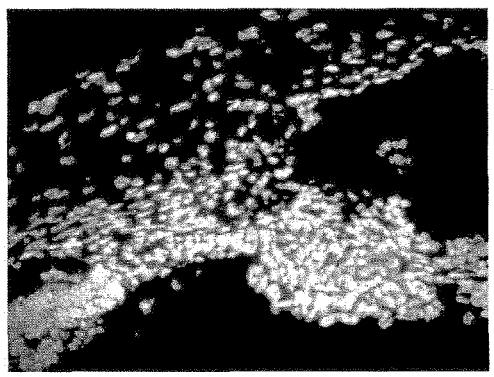
Figure 1J:
Figure 1K:
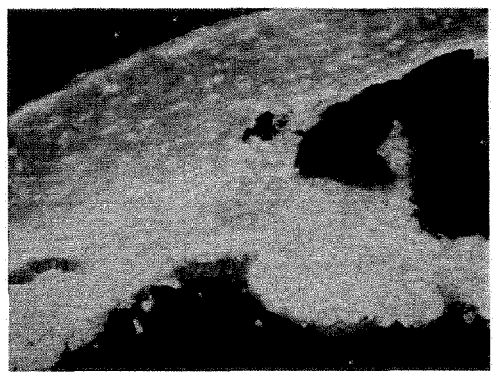
Figure 1L:
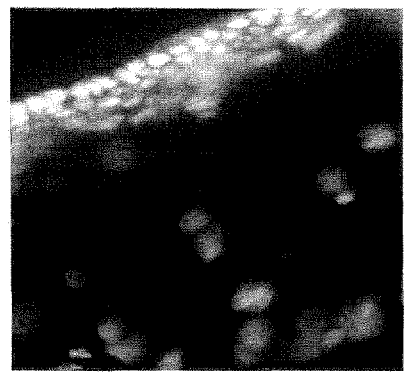
Figure 1M:
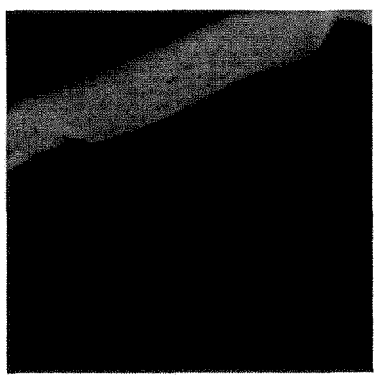
Figure 1N:
Figure 1O:
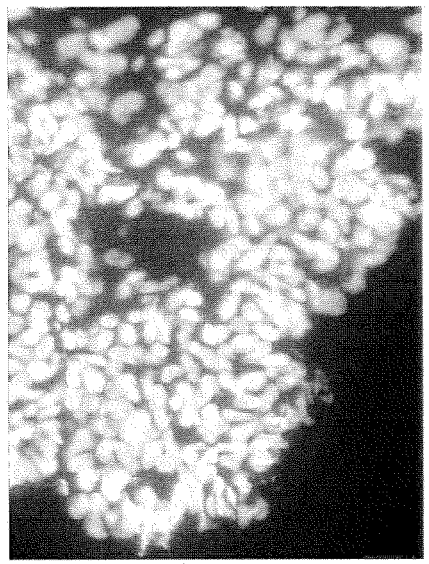
Figure 1P:
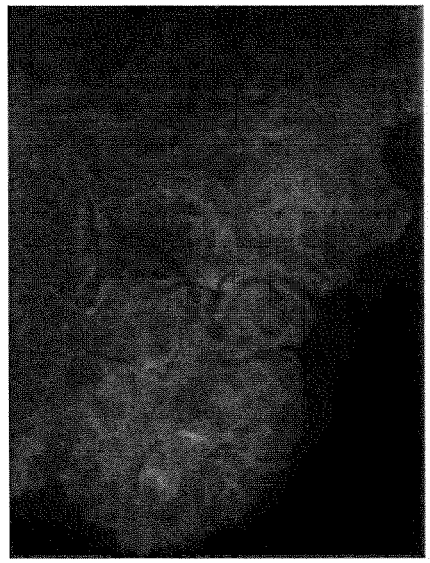
Figure 1Q:
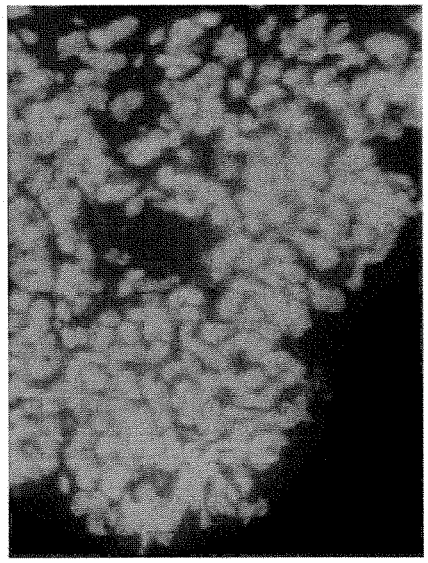
Figure 2A:
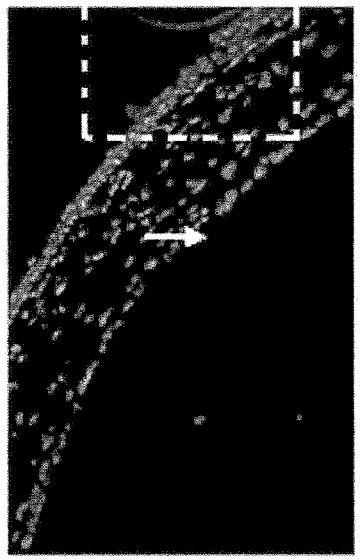
FIG. 2 shows immunohistochemistry images of the central (a-d) and peripheral cornea (e-j), 24 hours after 5 instillations of AC-8 demonstrating the penetration of the Fab through a transcleral route.
Figure 2B:
Figure 2C:
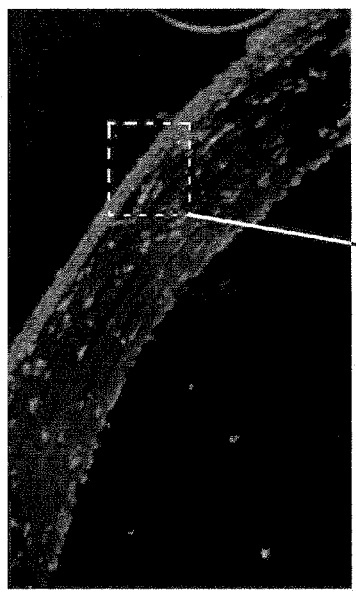
Figure 2D:
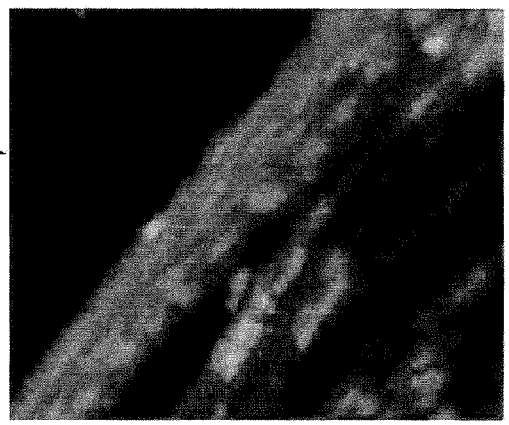
Figure 2E:
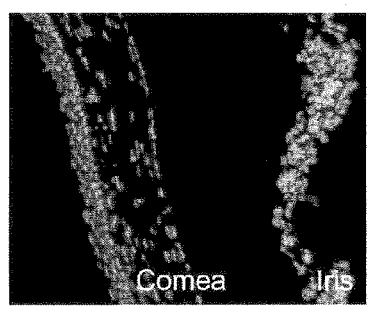
Figure 2F:
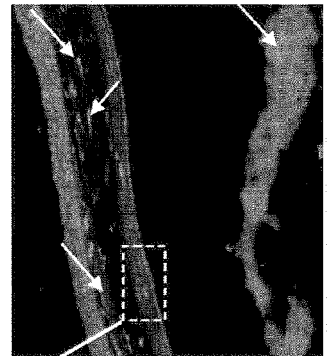
Figure 2G:
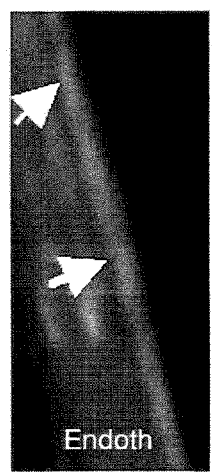
Figure 2H:
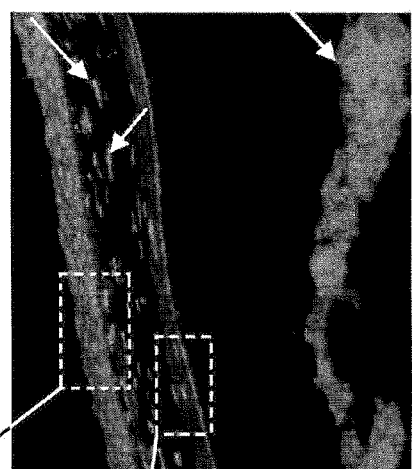
Figure 2I:
Figure 2J:
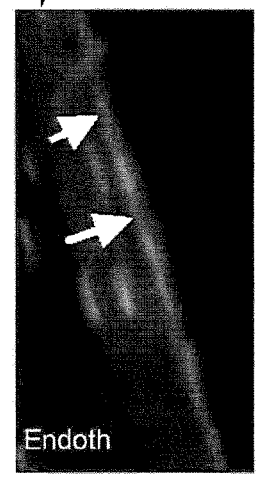
Figure 2K:
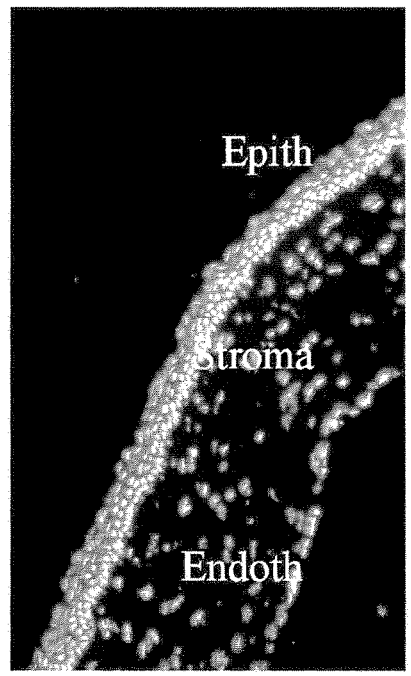
Figure 2L:
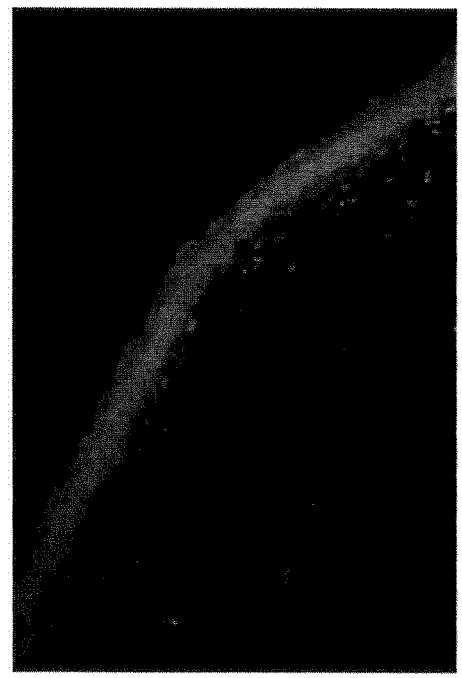
Figure 2M:
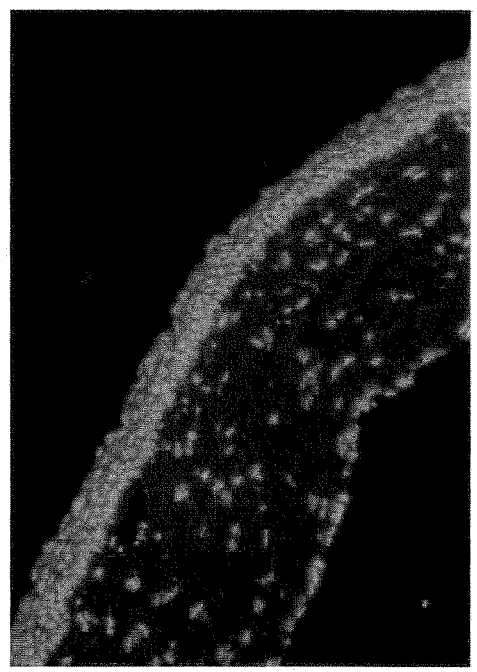

Immunohistochemistry on cornea following treatment with AC-8 5 times a day for 4 days and once on the fifth day. The results were compared to the vehicle group 6. When AC-8 is instilled 5 times a day for 4 days, at a concentration of 10 µg/ml (FIG. 1, a-k), an intense penetration of AC-8 is observed in the periphery of the cornea (FIG. 1 e-h), as well as in the anterior stroma in the centre of the cornea (FIG. 1 a-d). The penetration of AC-8 is much higher in the periphery of the cornea, the limbus and in the ciliary body than in the centre of the cornea, suggesting that AC-8 penetrates into the eye through a transcleral pathway, and then diffuses in the cornea. Again here, dendritic cells seem to have engulfed AC-8 since dendritiform cells positively stained with AC-8 are located in the sub-epithelial stroma (FIG. 1d). In the retina, AC-8 is located in the astrocytes at the inner retinal border.

Group 4 "SCJ1" (Day 0: 1 sub-conjunctival injection of AC-8, 10 µg/ml, sacrifice 1 hour after).

A single sub-conjunctival injection of AC-8 results in a very strong staining of AC-8 in both the anterior segment and the posterior segment of the eye. The results were compared to the vehicle group 7. In the cornea, AC-8 is concentrated in the epithelium and in the stroma as a diffuse staining as well as located in corneal cells.

In the ciliary body, AC-8 seems to have penetrated and is accumulated in epithelial cells. In the retina, AC-8 is clearly located in glial cells (astrocytes as well as Müller glial cell prolongations). In the retinal pigmented epithelial cells (RPE cells), a strong signal is also observed.

Group 5 "SCJ6" (Day 0: 1 sub-conjunctival injection of AC-8, 10 µg/ml, sacrifice 6 hours after).

In the cornea, AC-8 seems to be partly remaining essentially in the stroma. In the ciliary body, the fluorescent signal is reduced when compared to Group 4, but the limbus is still stained at this timepoint. In the retina, AC-8 signal is not present in glial cells and astrocytes anymore. In the retinal pigmented epithelial cells (RPE cells), the signal is also reduced. The results were compared to the vehicle group 7.

In these experiments the internal control omitting the first antibody were negative and showed very limited non specific background, contrarily to PBS treated eyes which showed some non specific background.

The analysis of the samples by IHC detection suggests that AC-8 can be detected using specific immunohistochemistry protocols. After instillation of AC-8 10 µg/ml on normal corneas, the antibody:

is not detected in the cornea or in any of the eye tissues 1 hour after single instillation;
is detected in the cornea after 5 instillations, a low signal is observed in the ciliary body and no signal can be detected in the retina;
is strongly located in the cornea, the ciliary body and in the retina, when instilled 5 times a day for 4 days.

When corneal penetration is observed, two types of staining are detected: one diffuse staining located in the stroma and the other concentrated staining in sub-epithelial corneal cells (keratocytes or dendritic cells). Since AC-8 is observed in cells in the sub-epithelial stroma in normal corneas and in cells in the whole stromal thickness in de-epithelialised cornea (see following examples), it is possible that AC-8 is phagocytosed in dendritic cells.

One hour after a single sub-conjunctival injection of AC-8 10 µg/ml, the antibody is located not only in the cornea but is also observed in the ciliary body and in the astrocytes and glial cells of the retina. Using this route of administration, deep external layers of the retina (Retinal Pigment Epithelial cells) are also stained. Staining is stronger at the periphery of the cornea than in the centre, as observed after instillation. Six hours after a single sub-conjunctival injection of AC-8 10 µg/ml, the antibody has almost been eliminated from the eye: it remains slightly in the cornea and the limbus but is not detectable anymore in the ciliary body nor in the retina.

In conclusion, these observations suggest that AC-8 can penetrate inside the ocular tissues of the eye through an intact cornea or through its adjacent limbus, and this penetration may be observed at the 10 µg/ml concentration.

AC-8 seems to penetrate through a transcleral route in the limbus, explaining retinal penetration and strong staining at the periphery of the cornea. AC-8 is engulfed in corneal cells that can correspond to dendritic cells or keratocytes. Whether AC-8 causes dendritic cell activation remains to be clarified.

Example 3

AC-8 Penetrates into the Intact Eye and can be Detected by Using ELISA Testing at One Hour after Instillation in the Aqueous Humour and in the Vitreous Sixty (60) pigmented rats from Brown Norway strain will be randomly divided into ten (10) groups of six (6) animals.

For the topical administrations (groups 1 to 8), the animals received 10 µl of test items or vehicles in both eyes 5 times a day.

For the sub-conjunctival administrations (groups 9 and 10), the animals received a single injection of 50 it of test item 1 in both eyes.

The table below summarizes the allocation of animals in treatment group:

| Group | Route of administration | Treatment | Time-points after the last administration | Number of animals |
|---|---|---|---|---|
| 1 | 5 × instillation | AC-8 Fab (1 mg/ml) | 1 h | 6 with administration in both eyes |
| 2 | | | 6 h | |
| 3 | | AC-8 Fab (0.5 mg/ml in PBS) | 1 h | |
| 4 | | | 6 h | |
| 5 | | AC-8 Fab (0.5 mg/ml in Vismed ®) | 1 h | |
| 6 | | | 6 h | |
| 7 | | PBS (vehicle 1) | 1 h | |
| 8 | | PBS/Vismed ® (vehicle 2) | 1 h | |
| 9 | 1 × subconjunctival injection | AC-8 Fab (1 mg/ml) | 1 h | |
| 10 | | | 6 h | |

At the corresponding time-points, animals were anesthetized. Whole blood was sampled for serum preparation. After euthanasia, aqueous humour (AH), corneal epithelium (Cepi), corneal stroma+endothelium (Cstr+end), vitreous (V) and retina (R) were sampled from both eyes and pooled for each animal for Elisa analyses Route and Method of Administration. For groups 1 to 8, test item or vehicles were instilled 5×10 µl during the day (8 am to 4:00 pm) in both eyes using an appropriate micropipette.

For groups 9 to 10, animals received under anaesthesia (i.m. injection of xylazine 5 mg/kg; ketamine 25 mg/kg) a single subconjunctival injection (50 µl) in both eyes.

At the time-points listed in the table above, animals were anesthetized by an intramuscular injection of a mix solution of Rompun® (xylazine 5 mg/kg) and Imalgene® 1000 (ketamine 25 mg/kg).

Approximately 2 ml of blood were removed by cardiac puncture just before sacrifice. 600 µl of serum for each animal were stored at −80° C. until Elisa assay.

Animals were euthanized by a cardiac injection of overdosed pentobarbital.

Immediately after sacrifice, aqueous humour (AH), corneal epithelium (Cepi), corneal stroma+endothelium (Cstr+end), vitreous (V) and retina (R) were quickly and carefully dissected from both eyes from 2 rats. Ocular structures from both eyes were pooled for each animal from each group.

Figure 4:
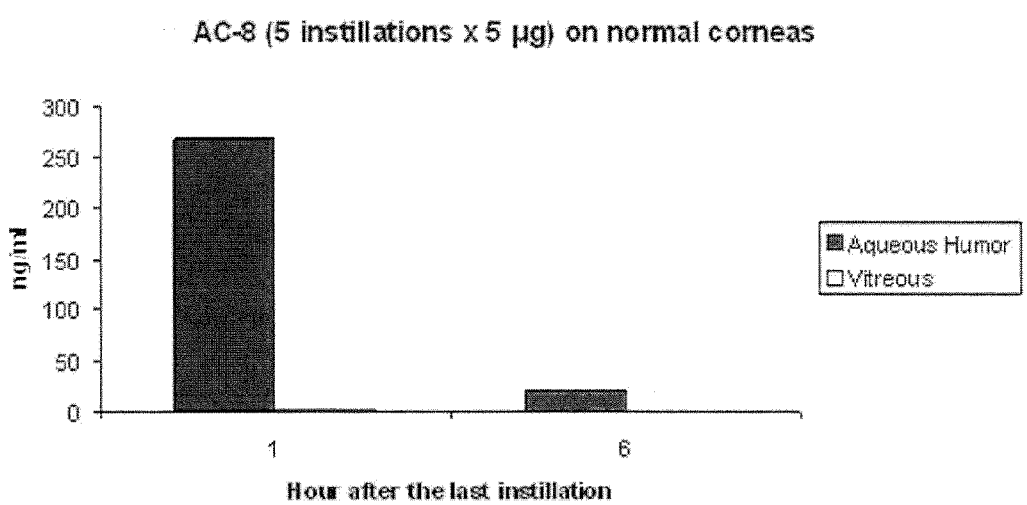
FIG. 4 is a histogram showing the concentration of AC-8 in aqueous and vitreous humours of mice with normal corneas 1 and 6 hours after 5 instillations of 5 μg AC-8.

Results of Ac-8 concentrations in the aqueous humour and vitreous humour are shown in FIG. 4.

Example 4

After De-Epithelialisation of the Cornea, the Ocular Penetration is Enhanced in the Aqueous Humour and in the Vitreous This set of experiments was carried out to evaluate the Fab's biodistribution when topically administered onto rat de-epithelialised corneas and during the reepithelialisation phase of the corneas. The experiment allowed evaluation of the Fab's penetration into the cornea during cicatrisation of a cornea-ulcer penetration of AC-8 Fab fragment topically administered.

The substance tested was as described above, but concentration was 100 µg/ml. Animals were as described above. Instillation or sub-conjunctival injection was carried out in one eye instead of both eyes.

On Day 0, one eye of each animal was de-epithelialised on a calibrated corneal area, under general anaesthesia (xylazine+ketamine) and local anaesthesia, using a calibrated biopsy punch and a surgical knife. For ethical reasons, the corneal ulcer model and the subsequent treatment were only performed on one eye per animal. The controlateral eye must be left untouched. 5 rats (5 eyes, right eyes only) per group were used. Animals were administered as follows:

| Groups (n = 3) | Group code | Adm. substance | Administration route | Day 0 | Day 1 | Day 2 | Sacrifice |
|---|---|---|---|---|---|---|---|
| 1 | H5 | AC-8 Fab | Instillation | 5 (1/hour) | — | — | Day 0: 1 hour after the 5$^{th}$ instillation |
| 2 | H29 | AC-8 Fab | Instillation | 5 (1/hour) | — | — | Day 1: 24 hours after the 5$^{th}$ instillation |
| 3 | D2 | AC-8 Fab | Instillation | 5 (1/hour) | 5 (1/hour) | 1 | Day 2: 1 hour after last instillation |
| 4 | SCJ1 | AC-8 Fab | Sub-conjunctival injection | 1 | — | — | Day 0: 1 hour after injection |
| 5 | SCJ6 | AC-8 Fab | Sub-conjunctival injection | 1 | — | — | Day 0: 6 hours after injection |
| 6 | SCJ24 | AC-8 Fab | Sub-conjunctival injection | 1 | — | — | Day 1: 24 hours after injection |
| 7 | C-D2 | Vehicle | Instillation | 5 (1/hour) | 5 (1/hour) | 1 | Day 2: 1 hour after last instillation |
| 8 | C-SCJ | Vehicle | Sub-conjunctival injection | 1 | — | — | Day 0: 1 hour after injection |

Sampling is summarized in the following table:

| Groups 1 to 8 | Rat 1 | Rat 2 | Rat 3 | Rat 4 | Rat 5 | Total samples | Analyses |
|---|---|---|---|---|---|---|---|
| Aqueous humour | 1 treated eye | 1 treated eye | 1 treated eye | 1 treated eye | — | 32 | Elisa |
| Vitreous humour | 1 treated eye | 1 treated eye | 1 treated eye | 1 treated eye | — | 32 | Elisa |
| Corneas | 1 treated eye | 1 treated eye | 1 treated eye | 1 treated eye | — | 32 | Elisa |
| Retinas | 1 treated eye | 1 treated eye | 1 treated eye | 1 treated eye | — | 32 | Elisa |
| Complete eye | — | — | — | — | 1 eye | 8 | IHC |
| Serum | 1-2 mL | 1-2 mL | 1-2 mL | 1-2 mL | 1-2 mL | 40 | Elisa |

4 rats (4 treated eyes) of each group (1 to 8) were used to collect aqueous and vitreous humours, serum and neuroretinas, for ELISA testing. Serum samples (approximately 1-2 mL) were taken from the 5 rats of each group 1 to 8, just before sacrifice. A total of 32 samples of aqueous humour (approximately 10-20 μL) and vitreous humour (approximately 20-30 μL), 32 samples of corneas and retinas and 40 serum samples were collected in screw capped Eppendorf® containers and stored at −80° C.

Both eyes of the fifth rat of each group (total 16 samples) were fixed and prepared for cryosectioning.

Cryosections were used for immunohistochemical (IHC) analyses with labelled antibodies in order to determine distribution of AC-8 Fab within the cornea layers and the ocular globe.

The frozen cryosections (10 μm) were treated as follows:
fixed 15 minutes in paraformaldehyde 4% at room temperature (RT),
rinsed twice 10 minutes in PBS 1× at RT,
rinsed 2×10 minutes in PBS-Triton™ X-100 0.1% at RT,
incubated overnight at +4° C. with goat anti-human IgG (Pierce #31132, 1/50 in PBS-Triton™ X-100 0.1%) excepted for the control incubated in PBS 1× only,
rinsed 3×10 minutes in PBS-Triton™ X100 0.1% at RT,
incubated 1 hour at +20° C. in the dark with Molecular Probes donkey anti-goat IgG (H+ L)—Alexafluor® 594 (red) 1/50,
rinsed twice 10 minutes in PBS 1× at RT,
incubated in DAPI (4',6'-diamidino-2-phenylindole) (blue) 1/5000 in PBS 1×, for nuclear labelling, 5 minutes in the dark at RT,
rinsed 5×5 minutes in PBS 1× at RT,
rinsed once 10 minutes in distilled water at RT and dried,
placed on microscope slides for lecture using a Fluorescence Microscope (Olympus).

The nuclei were stained in blue with DAPI, and the anti-human IgG antibodies, used to reveal AC-8, appear in red (secondary antibody Alexa Fluor® 594-labeled).

Group 1 "H5" (Day 0: 5 instillations of AC-8 100 μg/mL, sacrifice 1 hour after the last one).

AC-8 is detected clearly in the centre (especially at the junction between epithelialised-de-epithelialised areas) and at the periphery of the cornea: AC-8 concentrates in the sub-epithelial space at the border of the ulceration. Interestingly, AC-8 penetration is also observed at the periphery of the cornea, in the sub-epithelial space. In the corneal endothelium, AC-8 can not be detected in the central area, but is slightly detectable in the peripheral area. Immunohistochemistry of the control PBS-treated cornea displays very little background.

In the limbus AC-8 is located in the ciliary body and also in the iris. Note that AC-8 is also identified in vascular endothelial cells in the limbus.

This distribution of AC-8 on a de-epithelialised cornea shows that the penetration of the Fab occurs mainly through the limbus and a transcleral pathway, rather than through a direct trans-corneal penetration.

In group 1, very weak labelling of AC-8 is observed in the retina.

Group 2 "H29" (Day 0: 5 instillations of AC-8 100 μg/mL, sacrifice 24 hours after).

In Group 2, the corneal epithelium of the central cornea is almost completely reformed in all the examined sections (FIG. 2 a-j), with some irregularities at the surface of the reconstituted epithelium (white square FIG. 2 a). AC-8 remains located in cells in the sub-epithelial space. At the periphery of the cornea (FIG. 2 e-j), AC-8 is concentrated in the epithelium, the sub-epithelial space (FIG. 2 i arrows) and is accumulated in the endothelium (FIGS. 2 g and 2 j, arrowheads).

24 hours after 5 instillations, AC-8 has penetrated from the surface of the cornea into the deeper layer of the cornea and up to the endothelium. It is also clearly observed in the iris at this time point (FIGS. 2 f and 2 h arrows). Infiltrating cells containing AC-8 are located in the sub-epithelial space of the cornea (FIGS. 2 f and 2 h, arrows, FIG. 2 c, high magnification, FIG. 2 i, arrows). These cells could correspond to polymorphonuclear cells, macrophages or to dendritic cells.

In the limbus and ciliary body, AC-8 has penetrated through the epithelium and is located in the subepithelial area and in the ciliary body.

In group 2, AC-8 is detected in the peripheral retina but not in the central posterior retina. When compared to the control group 7, AC-8 seems to be located in the nuclear layers of the peripheral retina.

Group 3 "D2" (Day 0 to Day 1: 5 instillations per day of AC-8 100 μg/mL, Day 2: 1 instillation, sacrifice 1 hour after).

In Group 3, the epithelium is totally reformed and instillation has been continued during the scaring period. AC-8 is detected very strongly in the corneal epithelial cells, in stromal cells and weakly in the endothelium when compared to vehicle control group.

Examination of the limbus in group 3 and the anterior retina shows that AC-8 has penetrated deeply in the ciliary body when compared to the vehicle control group. AC-8 is identified in the ciliary body epithelium.

In group 3, a significant staining for AC-8 is noted in the peripheral but not in the posterior (central) retina. Interestingly, AC-8 seems to have diffused in all retinal layers, as well as in the RPE cell layer.

When compared to the penetration of AC-8 on intact cornea (see above), it seems that ulceration of the epithelium has enhanced the retinal penetration of AC-8.

Group 4 "SCJ1" (Day 0: 1 injection of AC-8 solution, 100 μg/mL, sacrifice 1 hour after), Group 5 "SCJ6" (Day 0: 1 injection of AC-8 solution, 100 μg/mL, sacrifice 6 hours after), Group 6 "SCJ24" (Day 0: 1 injection of AC-8 solution, 100 μg/mL, sacrifice 24 hours after).

One single injection of AC-8 in the sub-conjunctival space is efficient to allow AC-8 penetration in the periphery of the cornea at 1 hour, 6 hours and 24 hours.

The penetration of AC-8 after sub-conjunctival injection is stronger in the periphery of the cornea than in the centre of the cornea, where it remains weak at all time points even in the ulcerated corneas (Group and Group 5). Reformation of the integrity of the epithelium does not influence AC-8 distribution in all corneal layers and in the iris at 24 hours (Group 6).

In the limbus and the ciliary body, AC-8 is homogenously distributed as observed in groups 4 and 5, with an additional concentration of AC-8 in the limbal sub-epithelial region in group 6. Sub-conjunctival injection is also efficient to allow the penetration of AC-8 in an eye with a corneal ulceration, not only in the retinal layers at the periphery of the retina but also, but more weakly, in the posterior region of the retina at 1 hour (group 4), 6 hours (group 5) and 24 hours (group 6). At 24 hours, AC-8 is mostly concentrated at the periphery of the retina (group 6).

In the retina, AC-8 is detected as patchy concentration of staining in retinal cells, but AC-8 is not homogenously distributed in the entire retina.

ICH observations are summarized in the following table:

| | CORNEA | | | | | | LIMBUS/ CILIARY BODY | | RETINA | |
|---|---|---|---|---|---|---|---|---|---|---|
| | Central (ulcerated zone) | | | Periphery | | | Iris/ | | | |
| | epith | stroma | endoth | epith | stroma | endoth | cb | limbus | periph | post |
| Group 1 (5 inst, 1 h) | − | +++ | − | − | +++ | +/− | +++ | +++ | − | − |
| Group 2 (5 inst, 24 h) | − | + | − | ++ | ++ | + | − | + | +/− | − |
| Group 3 (5 inst, 5 inst, 1 inst, 1 h) | ++ | + | − | ++ | +++ | − | ++ | ++ | + | − |
| Group 4 (1 sub-conj, 1 h) | − | −/+ | − | + | + | +/− | ++ | ++ | + | +/− |
| Group 5 (1 sub-conj, 6 h) | +/− | − | − | ++ | +++ | ++ | ++ | ++ | + | +/− |
| Group 6 (1 sub-conj, 24 h) | − | − | − | +/− | ++ | − | +++ | +++ | + | +/− |

-continued

| | CORNEA | | | | | | LIMBUS/ CILIARY BODY | | RETINA | |
| | Central (ulcerated zone) | | | Periphery | | | Iris/ | | | |
| | epith | stroma | endoth | epith | stroma | endoth | cb | limbus | periph | post |
|---|---|---|---|---|---|---|---|---|---|---|
| Group 7 - Control (5 inst, 5 inst, 1 inst, 1 h) | – | – | – | – | – | – | – | – | – | – |
| Group 8 - Control (1 sub-conj, 1 h) | – | – | – | – | – | – | – | – | – | – |
| Control without primary antibody | – | – | – | – | – | – | – | – | – | – |

During the re-epithelialisation process, instillation of AC-8 does not delay scaring of the cornea, when compared to the control and does not enhance significantly any clinical or histological inflammatory reaction.

Penetration of AC-8 in the cornea (epithelium, stroma and endothelium) is observed mainly at the periphery of the cornea and in the limbus. AC-8 is detected in corneal cells (epithelium and endothelial cells as well as stromal cells) and is also observed in sub-epithelial infiltrating cells that could result from a local immunological reaction to AC-8 injection (AC-8 being recognized as a foreign—human—protein).

AC-8 penetrates also in the iris, ciliary body and peripheral retina at later time point, suggesting diffusion from the outer to the inner tissues of the eye. It is interesting to note that AC-8 is also observed in the vascular endothelium of endothelial cells, implying that a systemic diffusion of AC-8 could potentially occur.

Localisation of AC-8 in the different regions of the cornea clearly shows that AC-8 penetration occurs mostly through a transcleral pathway, even when an ulcer is present at the centre of the epithelium.

Instillation of AC-8 should be able to penetrate the cornea at all stages of herpes keratitis, even when corneal epithelium is reforming.

Sub-conjunctival injection is as efficient as repeated instillations of AC-8 to target the cornea.

Penetration of AC-8 in the cornea seems to follow the same transcleral pathway using either instillation or sub-conjunctival injection.

Sub-conjunctival injection is more efficient than repeated instillations to target the ciliary body and the retina.

Figure 5:
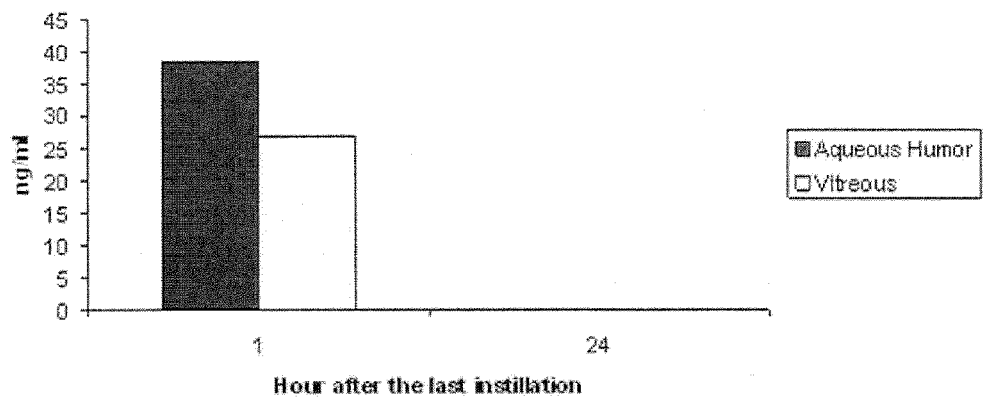
FIG. 5 is a histogram showing the concentration of AC-8 in aqueous and vitreous humours of mice with de-epithelialised corneas 1 and 24 hours after 5 instillations of 5 μg AC-8.

The ELISA results obtained on aqueous humour and vitreous humour of de-epithelialised cornea are summarised in FIG. 5. As may be noted from the figure, AC-8 quantification into both aqueous and vitreous humours demonstrates an efficient penetration into the eye.

In conclusion, from the present distribution study performed on ulcerated cornea, it appears that 5 instillations per day is non toxic on de-epithelialised cornea.

After 5 instillations per day, AC-8 remains located in corneal cells for 24 hours, and penetrates in deep corneal layers as well as in iris and ciliary body.

Penetration of AC-8 is mostly observed through the limbus and a transcleral pathway, suggesting that AC-8 will be able to penetrate the cornea at all stages of herpes keratitis, even when the epithelium is reformed.

The invention claimed is:

1. A method of treating a herpes simplex virus related (HSV-related) ocular disease in vivo comprising administering topically or by subconjunctival injection an effective amount of a fully human antigen binding fragment of an antibody comprising the sequence set out in SEQ ID NO: 1 and SEQ ID NO: 2
    wherein detection of binding of the antigen binding fragment to antigen is indicative of the ocular disease, and wherein the administering treats the ocular disease.

2. The method of claim 1, wherein said antibody is formulated in a composition comprising a retention enhancer.

3. The method of claim 2, wherein the retention enhancer is selected from the group consisting of sodium hyaluronate, hydroxymethylcellulose, hydroxyethyl cellulose, hydroxyethylmethylcellulose, hydroxypropylmethylcellulose, vinylpolyalcohol, xantan gum, gellan gum, chitosan, polylactic acid and derivatives thereof.

4. The method of claim 1, wherein the antibody is administered in the form of an eye drop, ointment, gel, ophthalmic cream.

5. The method of claim 1, wherein the antibody has a detectable label associated therewith.

* * * * *